United States Patent
Jansen (10) Patent No.: US 10,280,471 B2
(45) Date of Patent: May 7, 2019

(54) METHODS FOR DETECTING MICRO-ORGANISMS AND/OR BIOLOGICAL SUBSTANCES IN A FLUID

(71) Applicant: Biotrack Holding B.V., Sneek (NL)

(72) Inventor: Gijsbert Johan Jansen, Giekerk (NL)

(73) Assignee: Biotrack Holding B.V., Sneek (NL)

( * ) Notice: Subject to any disclaimer, the term of this patent is extended or adjusted under 35 U.S.C. 154(b) by 0 days.

(21) Appl. No.: 15/186,186

(22) Filed: Jun. 17, 2016

(65) Prior Publication Data
US 2016/0304939 A1    Oct. 20, 2016

Related U.S. Application Data

(63) Continuation of application No. 13/574,590, filed as application No. PCT/NL2011/050103 on Feb. 14, 2011, now abandoned.

(30) Foreign Application Priority Data

Feb. 12, 2010   (NL) ..................................... 2004238
Apr. 6, 2010   (WO) ................ PCT/NL2010/050176

(51) Int. Cl.
| | |
|---|---|
| *C12M 1/26* | (2006.01) |
| *G01N 21/64* | (2006.01) |
| *C12Q 1/24* | (2006.01) |
| *G01N 21/76* | (2006.01) |
| *C12M 1/34* | (2006.01) |
| *C12M 1/42* | (2006.01) |
| *C12Q 1/689* | (2018.01) |
| *C12Q 1/04* | (2006.01) |
| *G01N 35/00* | (2006.01) |
| *B01L 3/00* | (2006.01) |
| *G01N 35/10* | (2006.01) |

(52) U.S. Cl.
CPC .............. *C12Q 1/689* (2013.01); *B01L 3/502* (2013.01); *C12Q 1/04* (2013.01); *G01N 21/645* (2013.01); *G01N 21/6428* (2013.01); *G01N 35/00029* (2013.01); *G01N 35/10* (2013.01); *B01L 2300/0654* (2013.01); *B01L 2300/0681* (2013.01); *B01L 2400/04* (2013.01); *B01L 2400/0633* (2013.01)

(58) Field of Classification Search
CPC ........... C12Q 1/689; C12Q 1/04; B01L 3/502; B01L 2300/0654; B01L 2300/0681; B01L 2400/04; B01L 2400/0633; G01N 21/6428; G01N 21/645; G01N 35/00029; G01N 35/10
See application file for complete search history.

(56) References Cited

U.S. PATENT DOCUMENTS

| | | |
|---|---|---|
| 3,940,250 A | 2/1976 | Plakas et al. |
| 5,627,042 A | 5/1997 | Hirose et al. |
| 5,725,758 A * | 3/1998 | Chace .................. B01D 61/027 210/134 |

(Continued)

FOREIGN PATENT DOCUMENTS

| | | |
|---|---|---|
| WO | WO0146382 A2 | 6/2001 |
| WO | WO2010040371 A1 | 4/2010 |

*Primary Examiner* — William H. Beisner
*Assistant Examiner* — Danielle B Henkel
(74) *Attorney, Agent, or Firm* — Marcus C. Dawes; Daniel L. Dawes (57) ABSTRACT

Methods for detecting micro-organisms and/or biological substances in a fluid are provided.

14 Claims, 7 Drawing Sheets

(56) References Cited

U.S. PATENT DOCUMENTS

| | | | |
|---|---|---|---|
| 6,149,824 A | * | 11/2000 | Chace .................... B01D 61/02 210/167.01 |
| 6,312,943 B1 | | 11/2001 | Takahashi et al. |
| 2003/0092170 A1 | | 5/2003 | Pressman et al. |
| 2004/0173531 A1 | | 9/2004 | Hammond |
| 2005/0173315 A1 | | 8/2005 | Bosch et al. |
| 2005/0214737 A1 | | 9/2005 | Dejneka et al. |
| 2006/0257941 A1 | | 11/2006 | McDevitt et al. |
| 2007/0231844 A1 | | 10/2007 | Grinon et al. |
| 2009/0111167 A1 | | 4/2009 | Schann |

* cited by examiner

METHODS FOR DETECTING MICRO-ORGANISMS AND/OR BIOLOGICAL SUBSTANCES IN A FLUID

This application is a continuation of U.S. patent application Ser. No. 13/574,590 filed Oct. 5, 2012, which application is a 371 international of PCT Patent Application Serial No. NL2011/050103 filed Feb. 14, 2011, which application claims benefit of PCT Patent Application Serial No. NL2010/050176 filed Apr. 6, 2010 and NL Patent Application Serial No. 2004238 filed Feb. 12, 2010.

The present invention relates to an automatic fluid sample preparation module for preparing a fluid sample. More specifically, the module is used for preparing a fluid sample for detection and measurement of micro-organisms and/or biological substances.

In practice, detection of micro-organisms and/or biological substances is performed by taking a sample from a fluid or fluid stream and subsequently measuring and analyzing the sample in a laboratory. Each sample has to be handled manually, at least to some extent, which is labour intensive and slow.

Furthermore, in practice, the act of obtaining the sample may expose the laboratory worker in certain cases to unnecessary risks. Also, the preparation, measurement and analysis has to be performed by skilled personnel in specialized laboratories. This is a problem in non-clinical settings where detecting and measuring the amount of micro-organisms and/or biological substances is important. An example of such a setting is the shipping industry, where contaminated ballast water discharges may pose a risk to natural ecosystems around the water, and knowledge about the level and types of micro-organisms present in said ballast water may be very helpful.

SUMMARY

The object of the present invention is therefore to provide an effective and efficient fluid sample preparation module for automatically preparing a fluid sample, specifically for subsequent detection and measurement of micro-organisms and/or biological substances.

This object is achieved with the automatic fluid sample preparation module for automatically preparing a fluid sample for detection and measurement of micro-organisms and/or biological substances according to the invention, the module comprising:

an inlet for automatically obtaining a sample directly from a fluid or fluid stream to be analyzed;

preparation means for preparing the fluid sample from the sample, comprising first coupling means for coupling with the inlet; and an outlet for discharge of prepared fluid to measurement means, wherein the preparation means are provided such that micro-organisms and/or biological substances from one or multiple samples are accumulated in the prepared fluid sample.

Detection of micro-organisms and/or biological substances may comprise establishing whether micro-organisms and/or biological substances are present. Measuring may comprise detecting and/or quantifying. Analyzing may also comprise measuring, detecting and/or quantifying.

For example, the micro-organisms to be detected using the prepared fluid sample are Enterobacteriaceae, *Enterococcus* sp., *Escherichia coli*, *Gardnerella vaginalis*, *Klebsiella pneumonieae*, *Klebsiella oxytoca*, *Legionella* sp., *Legionella pneumofila*, *Proteus mirabilis*, *Pseudomonas aeruginosa*, *Staphylococcus aureus*, *Staphylococcus saprophyticus*, *Staphylococcus* sp. or *Streptococcus* sp.

The module can be provided as a stand-alone system for preparing a fluid sample or in combination with measurement means.

By providing an inlet for automatically obtaining a sample directly from a fluid or fluid stream to be analyzed, the module can run autonomously. At any given time the module can automatically obtain a sample directly from a fluid or fluid stream to be analyzed and prepare a fluid sample from the sample.

For example, the fluid or fluid stream comprises water, urine, sugar syrup or a beverage such as beer.

A sample of a fluid or fluid stream is obtained through the inlet. The preparation means obtain this sample through the first coupling means and prepare a fluid sample from the sample. Optionally, the preparation means comprise a solvent container and a pump to add a solvent to the sample. Further examples of preparation means include: a reagent container for addition of a reagent, a heater, a cooler, mixing means and pumps for pumping fluids within the module.

The fluid sample prepared by the module according to the invention comprises micro-organisms and/or biological substances from one or multiple samples obtained directly from a fluid or fluid stream. In other words, the fluid sample is prepared such that the micro-organisms and/or biological substances which are present in the one or multiple samples are, at least for the greater part, also present in the resulting fluid sample. This enables concentration of micro-organisms from multiple samples into a single fluid sample. The fluid sample can therefore be prepared in a way which enables a reliable subsequent measurement.

Furthermore, in the case of detecting micro-organisms, conventional systems for preparing a fluid sample often rely on pre-incubation of the micro-organisms in order to increase the number of micro-organisms to enable detection in a subsequent measurement. Due to this pre-incubation, these systems require considerable time for preparing a fluid sample, usually at least 24 to 48 hours, and generally are labour consuming. The module according to the invention provides a way for increasing the number of micro-organisms in a fluid sample to enable detection and measurement thereof which is faster, automatic and autonomous.

A further advantage of the automatic fluid sample preparation module according to the invention is that it automatically obtains a sample from a fluid or fluid stream to be analyzed. The invention provides a so-called in-process system: the module has direct access to a fluid or fluid stream of a process for preparation of a fluid sample for subsequent measurement and detection. For example, this enables obtaining a sample from a fluid or a fluid stream at a remote location and/or located in a hazardous environment.

An even further advantage is that the preparation module enables a periodical analysis of a fluid or fluid stream by taking samples at different times and preparing them for subsequent analysis.

In addition, it is possible to increase statistical accuracy by performing measurements and analysis on a set of samples obtained from the same fluid or fluid stream.

An even further advantage is that the module can be configured to automatically obtain samples from a plurality of fluids or fluid streams. Since the system is in-process and automatic, mistakenly interchanging fluid samples is avoided.

Furthermore, the module is portable, which is for example advantageous in situations in which automatic preparation of fluid samples is required at different locations at great distances from each other.

Therefore, the automatic fluid sample preparation module according to the invention enables an effective and efficient preparation of a fluid sample for the detection and measurement of micro-organisms and/or biological substances.

In a preferred embodiment of the invention, the module comprises a filter for retaining micro-organisms and/or biological substances.

By providing a filter for retaining micro-organisms and/or biological substances, an efficient and effective preparation means is obtained for accumulating the micro-organisms and/or biological substances from one or multiple samples.

For example, the filter comprises plasma-polished stainless steel, wherein the filter comprises holes having a diameter in the range of 0-1 µm.

By providing the filter of stainless steel, a high strength is ensured. The fact that the filter comprises plasma-polished stainless steel ensures that the filter is easy to clean and no or relatively less precipitate or deposit is formed on the filter. A filter can therefore by re-used after an simple cleaning procedure. The cleaning procedure can for example be performed using a conventional dish-washer.

By providing holes having a diameter in the range of 0-1 µm, the filter is optimal for filtering out micro-organisms, which typically have dimensions larger than 0.5 µm. Preferably the holes have a diameter of 0.5 µm.

In a further preferred embodiment, the filter comprises a crossflow filter.

For example, the crossflow filter comprises a elongated permeable sheath of a ceramic material, enclosing an inner channel. The permeable sheath is covered by an outer tubing of a plastic material.

The fluid can flow through the inner channel in the longitudinal direction of the filter. When an overpressure is created, the fluid is forced through the permeable membrane, i.e. in the transverse direction of the filter. The permeable membrane filters the fluid forced through it.

An advantage of providing a crossflow filter is that micro-organisms and/or biological substances are retained by the filter and carried along the fluid sample during filtration. When an overpressure is applied, the fluid will flow through the boundaries of the filter, while the fluid content is retained. This enables accumulating micro-organisms and/or biological substances.

Furthermore, a crossflow filter has an increase lifetime and a longer period of operation in comparison with a regular filter.

In addition, a crossflow filter allows for a continuous filtration process.

Therefore, by providing a crossflow filter, an effective and efficient means for accumulating the micro-organisms and/or biological substances is obtained.

In a preferred embodiment according to the present invention, the preparation module comprises communication means. The communication means can for example comprise GPRS, infra-red, cables or other wired or wireless communication means. Furthermore, the communication means may comprise control signals for controlling the module. For example, the control signals can be generated on the basis of subsequent measurement and analysis of the prepared fluid sample. This enables so called sample exploration, in which information obtained on the basis of a measurement is used to alter the preparation procedure to increase measurement accuracy and precision.

For example, if a measurement on a prepared fluid sample reveals that the concentration of micro-organisms and/or biological substances is too low to be detected, the automatic preparation module can be instructed to concentrate the contents of more samples from the source to be analyzed in the next fluid sample.

A further advantage of the communication means is that it enables remote control of the module. This is especially advantageous in situations in which the fluid or fluid stream from which to obtain a sample is located remotely, located in a hazardous environment or is otherwise difficult to access.

In a further preferred embodiment according to the present invention the inlet and the preparation means comprise:
  a first inlet for obtaining a sample from a fluid or fluid to be analyzed;
  a fluid chamber connected to the first inlet;
  fluid sample preparation means comprising a filter and one or more of the following components: a heater, a cooler, a pump, a piston and mixing means; and
  a first outlet for discharging a prepared fluid sample, the first outlet being connectable to the measurement means.

For example, the fluid chamber is provided as a fluid container. Preferably, the fluid chamber is provided as a conduit or a conduit system. Also preferably, the filter comprises a crossflow filter.

The fluid chamber obtains a sample from a fluid or fluid stream through the first inlet. A fluid sample is prepared using the fluid sample preparation means. A filter is provided for filtration of the fluid sample. A heater can be provided for heating the fluid sample, a cooler can be provided for cooling the fluid sample, a pump can be provided for example for pumping fluid in and out the fluid chamber or pumping fluid through the filter, a piston can be provided for example for pumping fluid through the filter and mixing means can be provided for mixing the fluid sample.

Embodiments of the invention may include a single element of the listed fluid sample preparation means, or a combination of these elements. The prepared fluid sample can be discharged through the first outlet, which is connectable to measurement means. In this manner, the prepared fluid sample can be transported to measurement means for subsequent measurement.

It is noted that a piston can function as a fluid chamber.

In an optional embodiment of the module according to the present invention, the module further comprises a second inlet and a second outlet, wherein the first inlet is provided at the same side of the filter as the fluid chamber. A solvent can be added to the system using the second inlet. For example, this enables dilution of the fluid sample.

A displacement fluid can be added to the system using the second inlet. This enables displacement of the fluids present in the system. For example, the fluids can be displaced to the second outlet for discharge of the fluids to a waste container.

The first inlet for obtaining a sample from a fluid of fluid stream to be analyzed is placed at the same side of the filter as the fluid chamber. The contents of the fluid sample which can not pass the filter, for example micro-organisms or biological substances, can therefore be concentrated in the fluid chamber.

When an inlet is provided at the opposite side of the filter in relation to the fluid chamber, it is possible to filter out any undesired contents from the fluid or fluid stream, so that these will be absent in the fluid sample.

In a further preferred embodiment according to the present invention the fluid sample preparation means comprise a modular container system, comprising one or more containers for holding reagents, processing fluids and/or fluorescent beads.

Adding a reagent to the fluid sample enables labelling the micro-organisms or biological substances. The reagents can for example comprise a Fluorescent In Situ Hybridization (FISH) reagent, an immuno-fluorescence reagent, a general DNA marking reagent or a bioluminescence reagent. The reagents add light emitting, absorbing or reflecting properties of the micro-organisms or biological substances. Existing light properties of the micro-organisms or biological substances may also be altered or effectuated by a reagent.

In addition, the processing fluids may comprise cleaning fluids for cleaning the different parts of the system.

The fluorescent beads have a known light emitting property. By preparing a fluid sample containing fluorescent beads, a reference for analysis of the measurement is obtained. The fluorescent beads enable a calibration procedure for measurement equipment connected to the module according to the invention.

An advantage of the modularity of the container system is that it enables adding, replacing or removing containers holding different reagents, processing fluids and/or fluorescent beads. Depending on the requirements of the measurement and analysis of a certain process, suitable reagents, processing fluids and/or fluorescent beads can be selected. The preparation module is therefore multi-purpose and can be used in multiple situations. A further advantage is that the containers can be easily replaced when empty or broken.

In a further preferred embodiment according to the present invention according to the invention one or more containers comprise at least one reagent from the group comprising:

a Fluorescent In Situ Hybridization (FISH);
an immuno fluorescence reagent;
a general DNA marking reagent; and
a bioluminescence reagent.

The fluid sample preparation means can add a single reagent, or multiple of reagents, to the fluid sample. Adding multiple reagents enables, for example, a measurement in which a general DNA marking reagent indicates the total number of micro-organisms and a FISH reagent indicates the number of a specific species. Therefore, the amount of this specific species present in the fluid sample can be expressed as a percentage of the total micro-organisms.

The invention further relates to an automatic analysis system for automatically preparing, measuring and analysing a fluid sample for detection and measurement of micro-organisms and/or biological substances, the system comprising the fluid sample preparation module as described above and a second module comprising measurement means.

The same effects and advantages apply in respect to the analysis system as those described in respect to the automatic preparation module.

Preferably, the measurement means comprise second coupling means for coupling them to the outlet of the preparation module to obtain a prepared fluid sample.

Preferably, the measurement is carried out using a light detector. The detector can for example detect and measure fluorescent light, (bio-) luminescent light, direct light and reflected light. In many cases the intensity of the light is proportional to the amount of micro-organisms and/or biological substances.

Preferably, the system comprises communication means, for example for remote control of the module. Further examples include a display, a light signal or a sound signal for communicating an alarm, for example.

An advantage of the communication means is that by generating a control signal, such as for example an alarm signal or a process control signal, the system can effectuate process control actions on the basis of the in-process measurement and analysis. This enables a relatively fast response to analysis results. This is especially advantageous in cases in which undesired and/or harmful micro-organisms and/or biological substances are detected.

In a preferred embodiment according to the present invention, the automatic analysis system comprises a first module comprising the inlet and the preparation means, and a second module comprising the measurement means.

Providing a modular system improves the flexibility of the system according to the invention. A module of the system can be replaced or altered without affecting the other modules in the system. For example, this may involve and improve repairs, maintenance and cleaning of the modules.

In case other characteristics of the system are required, the modularity of the system allows for an update of only those modules that have been altered.

The modularity further has the advantage that specific modules can be added or removed, depending on the fluid or fluid stream to be analyzed. Moreover, the modules can even be used separately. For example, in a situation in which the sample of the fluid or fluid stream does not require automatic preparation, the module comprising the measurement means can operate stand-alone.

In an embodiment according to the invention, the system further comprises a light source. The light source enables irradiation of the fluid sample, for example to induce fluorescence. Optionally, more than one light source is provided to increase the total intensity of the light or to irradiate the fluid sample with light of different wavelength and/or intensity, for example.

Preferably, the light source comprises a light emitting diode (LED). Advantages of LEDs include low costs, relatively high intensity, low energy consumption, narrow emission bandwidth and a stable intensity over time.

Preferably, according to the invention, a light detector is provided at an angle of substantially 90 degrees with respect to the light source.

By providing a light detector at an angle of substantially 90 degrees with respect to the light source, the light detector measures substantially no direct light from the light source. The measured light is therefore substantially originating from the micro-organisms and/or the biological substances only, resulting in an improved measurement. It is noted that in any of the embodiments of the invention multiple light detectors and light sources can be provided.

Optionally, a light detector is provided at an angle of substantially 180 degrees with respect to the light source, i.e. a light detector is provided facing the light source. This enables a measurement of the light absorbed by the fluid sample which can be related to the total amount of micro-organisms or biological substances in the fluid sample.

In a further embodiment according to the invention, the light source comprises at least one ultraviolet (UV) light emitting diode (LED). Typical reagents respond to ultraviolet light, and emit fluorescence light in the visible spectrum. Advantages of the use of an UV-LED include low costs, relatively high intensity, low energy consumption and narrow emission bandwidth.

In an embodiment according to the invention, the measurement means comprise:

a light detector, preferably in combination with:
a cuvette with a length, the cuvette comprising:
an inlet for obtaining the fluid sample; and
an outlet for discharging the fluid sample.

By providing a cuvette with an inlet for obtaining the fluid sample and an outlet for discharging the fluid sample, it is possible to automatically obtain the fluid sample from the preparation means and discharge this fluid sample after the measurement and analysis.

In a preferred embodiment according to the present invention the cuvette comprises flushing means. This has the advantage that the same cuvette can be used for several measurements. A further advantage is that the measurements will be clean, i.e. the fluid sample being measured is not polluted with a previous fluid sample.

In a preferred embodiment according to the present invention one or more of the light detectors comprise Charge Coupled Devices (CCDs) provided in an array extending substantially over the length of the cuvette.

Using a CCD as a light detector has the advantage of a large dynamical range and a high quantum efficiency. The CCD is therefore able to detect and measure both very low light levels and very high light intensities.

The advantage of using a CCD provided in an array extending substantially over the length of the cuvette is that the detection area is maximized. Light from the fluid sample is emitted in every direction. It is therefore advantageous to maximize the detection area, especially in the case of low light intensities.

In a preferred embodiment according to the present invention the measurement means further comprise a light filter for filtering light of a specific wavelength and/or a mosaic light filter.

A mosaic light filter is an array of light filters of different colour.

By providing a light filter in front of the light source, the fluid sample can be irradiated with light of a well-defined wavelength. This wavelength is determined by the filter. By providing a light filter in front of the light detector, the measured light comprises wavelengths in the wavelength region of interest only. This wavelength region is determined by the light filter.

An advantage of placing a light filter in front of the light source is that a band of wavelengths can be selected from the broad spectrum of the light source. For example, a red filter in front of a light source emitting white light will result in the irradiation of the fluid sample by red light.

An advantage of placing a light filter in front of the light detector is that those components of the light having wavelengths which are not in the wavelength region of interest can be filtered out. For example, in the case an ultraviolet light source is used for excitation of reagents sensitive to ultraviolet light, an UV blocking filter in front of the light detector will filter out the ultraviolet components of the lights, and consequently only the light emitted by the excited reagent is measured. Typical UV sensitive reagents emit fluorescence light in the visible spectrum. By blocking UV light before measuring, one ensures that only the fluorescence light (visible spectrum) is measured and substantially no light from the source (UV).

The light filters are removable, such that for every specific application the appropriate filter can be selected. Preferably, changing light filters is handled automatically.

In stead of a single coloured light filter, a multi-coloured light filter or a mosaic light filter can be used. This results in a multi-coloured or full colour image taken by the light detector. Subsequently, certain wavelengths from the detector image can be filtered out. Preferably, this is implemented as a software algorithm on a processing unit. For example, a full colour image is obtained using the light detector, after which the blue and red components are selected using an algorithm implemented in software.

Preferably, the system further comprises control means for controlling the light collection time of the light detector. An advantage of controlling the light collection time of the light detector is that, in cases of low light intensities, the light collection time can be increased, such that eventually more light is collected and a better measurement results.

It is noted that the measures from the described embodiments can be combined in any combination. Furthermore, aspects of the analysis system can optionally be incorporated in the preparation module.

The invention further relates to a method for automatically preparing a fluid sample for detection and measurement of micro-organisms and/or biological substances using an automatic sample preparation module.

The same effects and advantages apply in respect to such a method as those described in respect to the automatic preparation module.

In a preferred embodiment of the method according to the invention, the method comprises the steps of:
obtaining a sample directly and automatically from a fluid or fluid stream to be analyzed; and
preparing the fluid sample from the sample by selecting one or more preparation steps from the group comprising filtration, dilution, concentration, heating, cooling, mixing, pumping, adding a processing fluid and adding a reagent.

The preparation steps are selected on the basis of the specific application. The preparation steps can be programmed in an instruction set and for each specific application a different instruction set can be executed.

In a preferred embodiment according to the present invention, the method further comprises the step of flushing. Flushing improves the quality of the measurements.

Flushing comprises for example discharging a sample from the module to a waste container or cleaning the fluid chamber using a flushing fluid. This ensures that no residues are present during preparation of a fluid sample.

In a preferred embodiment the method further comprises performing measurements, preferably using a light detector and analyzing the measurements.

For example, this corresponds to a method for automatically preparing, measuring and analyzing a fluid sample using an automatic analysis system as described above. The same effects and advantages apply in respect to such a method as those described in respect to the automatic analysis system.

In a preferred embodiment according to the present invention, the method further comprises the step of calibration.

Calibration ensures that the measurement and analysis are independent of internal and/or external influences. An example of an external influence is ambient temperature, which can influence the response of many detectors. Performing a calibration step prevents discrepancies between the actual situation and the results of the measurement and the analysis.

In a preferred embodiment according to the present invention, the method comprises the steps of:
adding fluorescent beads to the fluid sample before performing a calibration measurement;
performing the calibration measurement by measuring the intensity of the light emitted by the fluorescent beads; and correcting measurements according to the relation between the light intensity measured in the calibration measurement and an expected light intensity.

The fluorescent beads emit light with a known intensity and with a known wavelength. By providing a filter in front of the detector, a measurement is performed in which only the wavelengths corresponding to the wavelength of the beads' fluorescent light is detected and measured. The measured intensity is compared to the expected intensity of the light emitted by the fluorescent beads. This information is used for correction of measurements (subsequent, preceding or coincident with the calibration measurement).

In a preferred embodiment according to the present invention the method further comprises measuring a total amount of micro-organisms and/or biological substances and measuring an amount of one or more types of micro-organisms and/or biological substances. The total amount of micro-organisms and/or biological substances can for example be measured by measuring the total absorption of the light with which the fluid sample is irradiated.

The same fluid sample can be used to perform a different measurement in which an amount of one or more types of micro-organisms and/or biological substances is detected, for example using a FISH reagent. The amount of the specific type of micro-organisms and/or biological substances can then be expressed as a fraction of the total amount of micro-organisms and/or biological substances.

BRIEF DESCRIPTION OF THE FIGURES

Further advantages, features and details of the invention are elucidated on the basis of preferred embodiments thereof, wherein reference is made to the accompanying drawings, in which.

DETAILED DESCRIPTION

Figure 1:
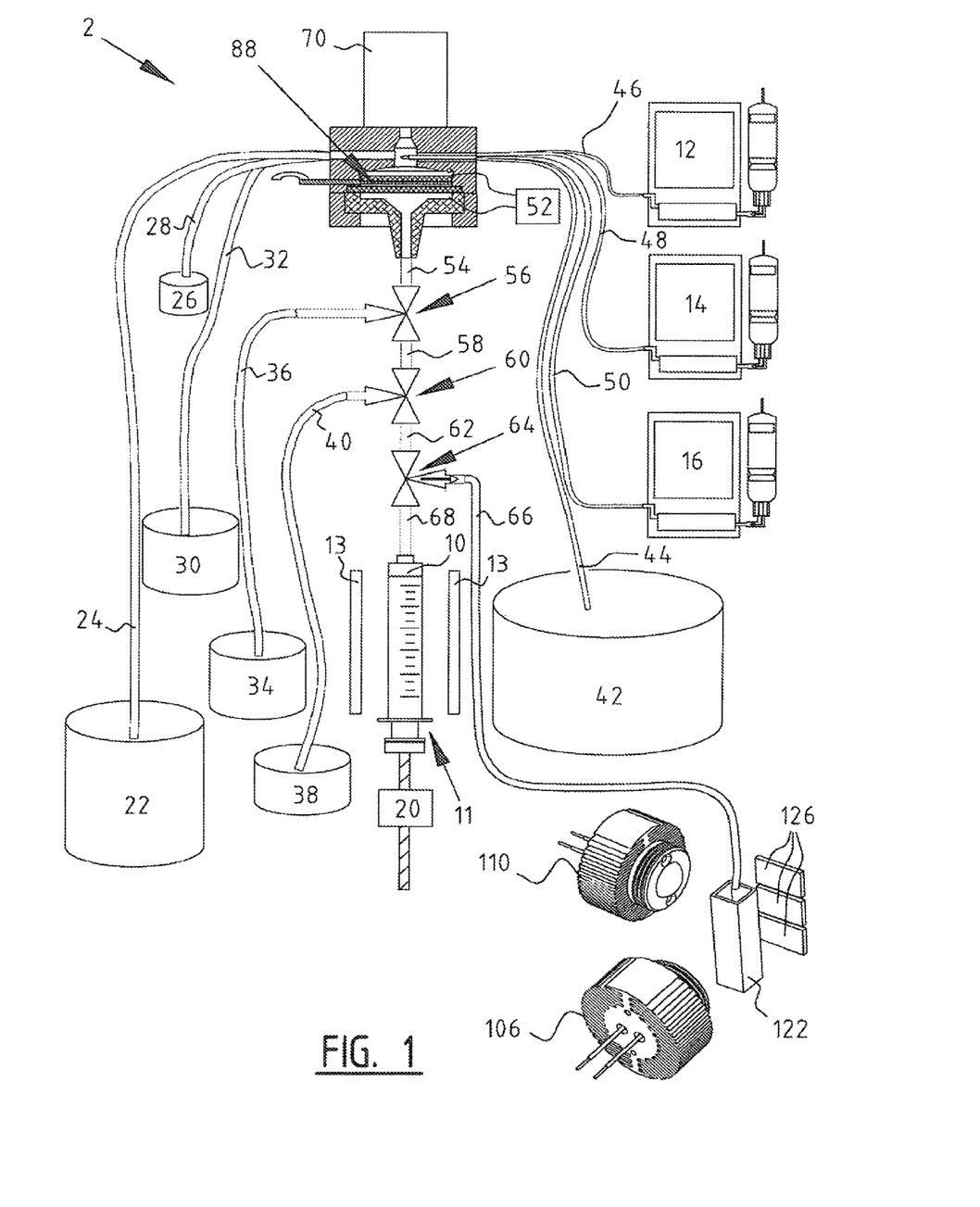
FIG. 1 shows a schematic representation of a first embodiment of an automatic analysis system according to the invention.
Figure 2:
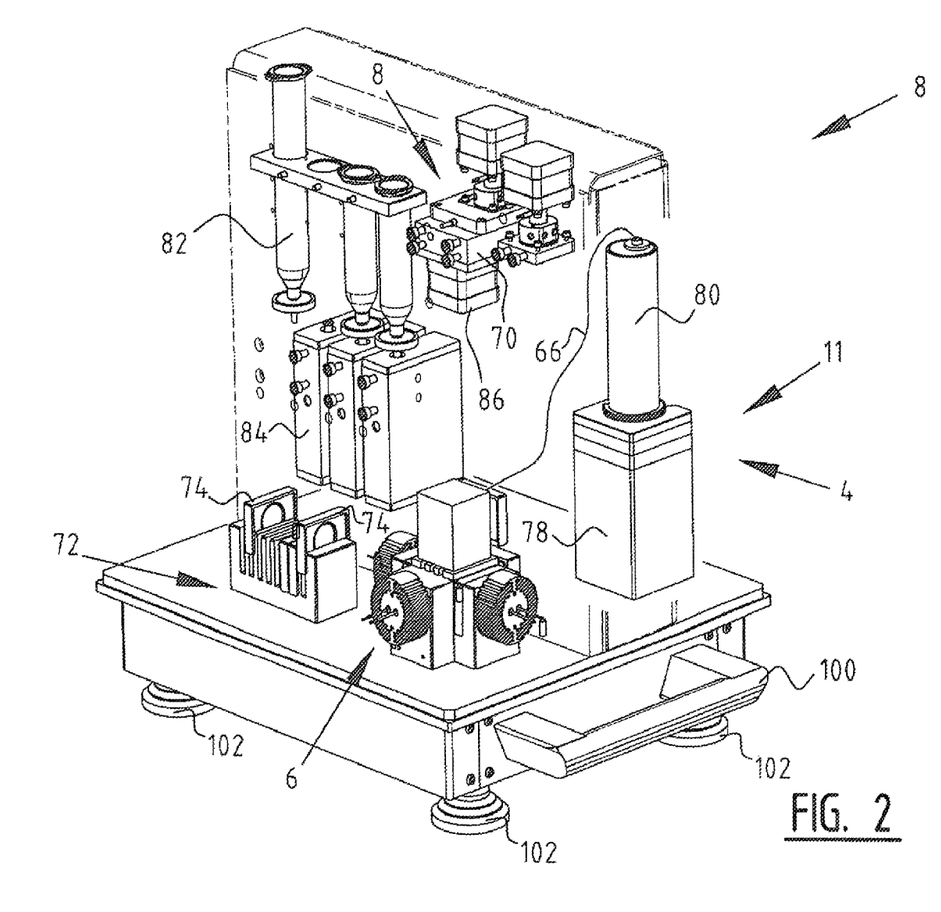
FIG. 2 shows a 3D drawing of the automatic analysis system according to FIG. 1.
Figure 3:
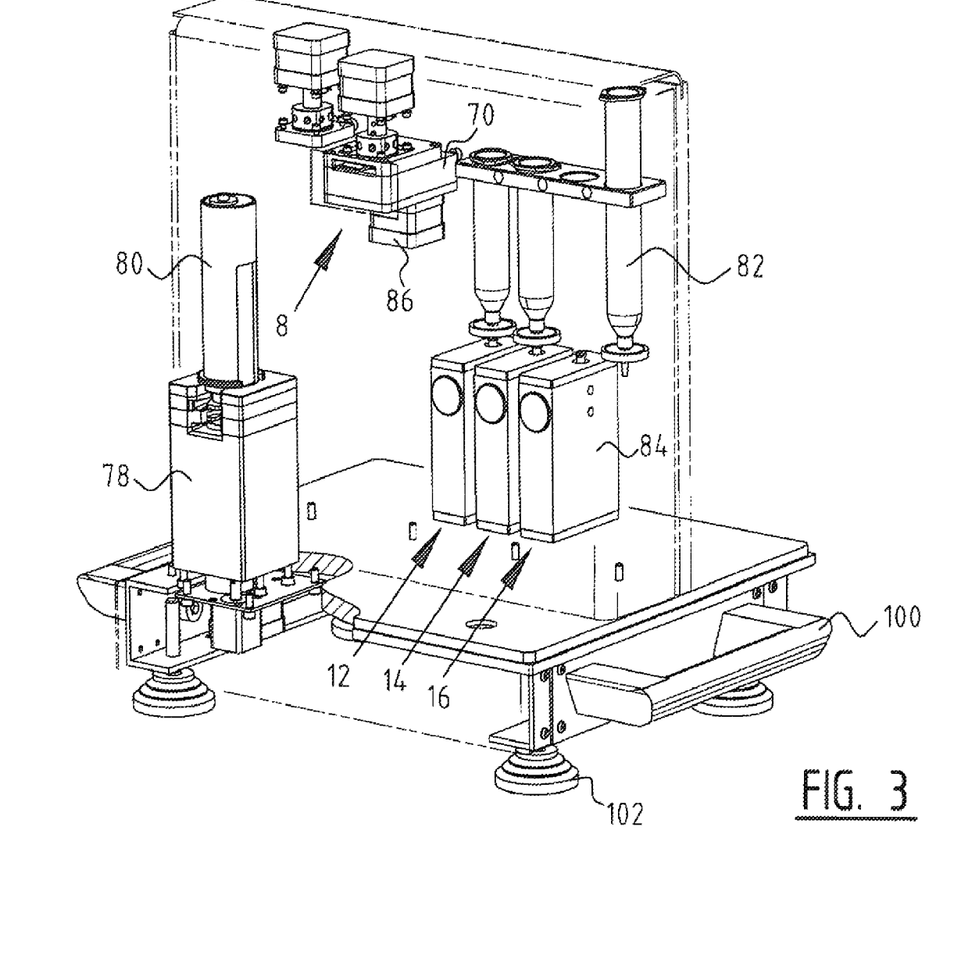
FIG. 3 shows a different view of the automatic analysis system of FIG. 2.

An automatic analysis system 2 comprises sample preparation means 4 and measurement means 6 (FIGS. 1, 2 and 3). In the illustrated first embodiment, the fluid sample preparation means 4 and the measurement means 6 are provided as modular units.

The fluid sample preparation means comprise a filter with inlet and outlets 8, a fluid chamber 11, a piston 10, containers 12, 14, 16, 22, 26, 34 holding reagents, processing fluids and/or fluorescent beads, a waste container 42, connecting pipes or tubes 32, 40 for connecting the preparation means to the fluids or fluid streams 30, 38 to be analyzed. The filter part 8, comprising a filter, an inlet and an outlet, is connected to the fluid chamber 11 through a series of valves 56, 60, 64.

A sample from the fluids or fluid streams 30, 38 flows through a tube 32, 40 to the fluid preparation chamber 11. A solvent can be added from the solvent container 22 through the tube 24. Optionally, instead of a solvent container also a direct connector to a water tap can be provided. Furthermore, a displacement fluid can be obtained from a displacement fluid container 26 through tube 28.

A connection 32 to a first fluid or fluid stream 30 is provided. The filter part 8 is connected to a waste container 42 through connection 44. Containers 12, 14, 16 are connected to the filter part 8 through connections 46, 48, 50. Container 34 is connected to the filter part 8 and the fluid chamber 11 through connection 36 and valve 56. A second fluid or fluid stream 38 is connected to the filter part 8 and the fluid chamber 11 through connection 40 and valve 60. Valve 64 and connection 66 connect the sample preparation means to the measurement means 6.

The piston 10 is operated by a motor 20. By operating the piston 10, the valves 56, 60, 68 and pumps (not shown), the fluid streams inside the system can be controlled. The fluid sample preparation means further comprise heating and cooling elements 18 which in the illustrated embodiment comprise a Peltier element/thermoelectric heat pump.

Figure 4:
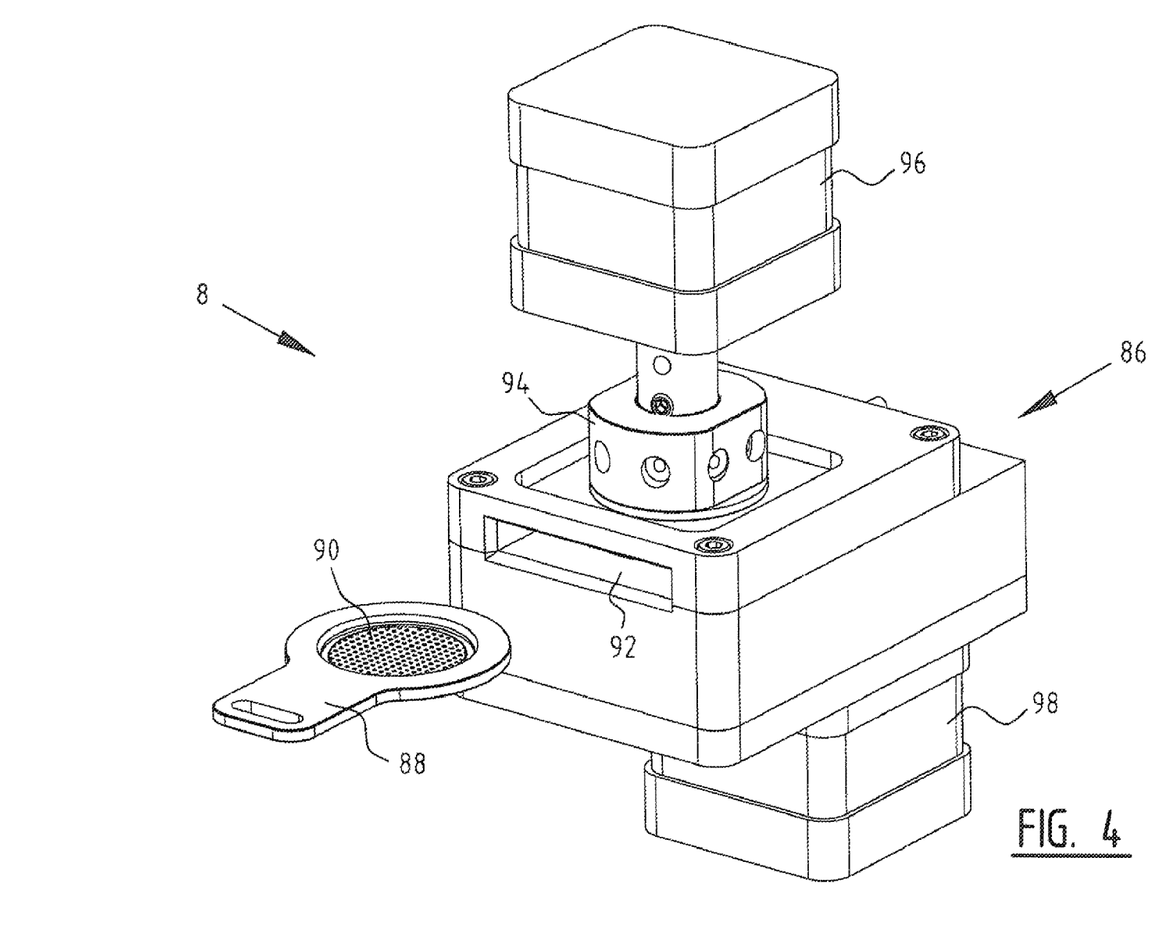
FIG. 4 shows the upper part of the fluid sample preparation means including a filter, according to the first embodiment.

FIG. 4 shows a close up of the filter 88, which comprises holes 90. The filter can be removed or inserted into the filter part 8 through slot 92.

Figure 5:
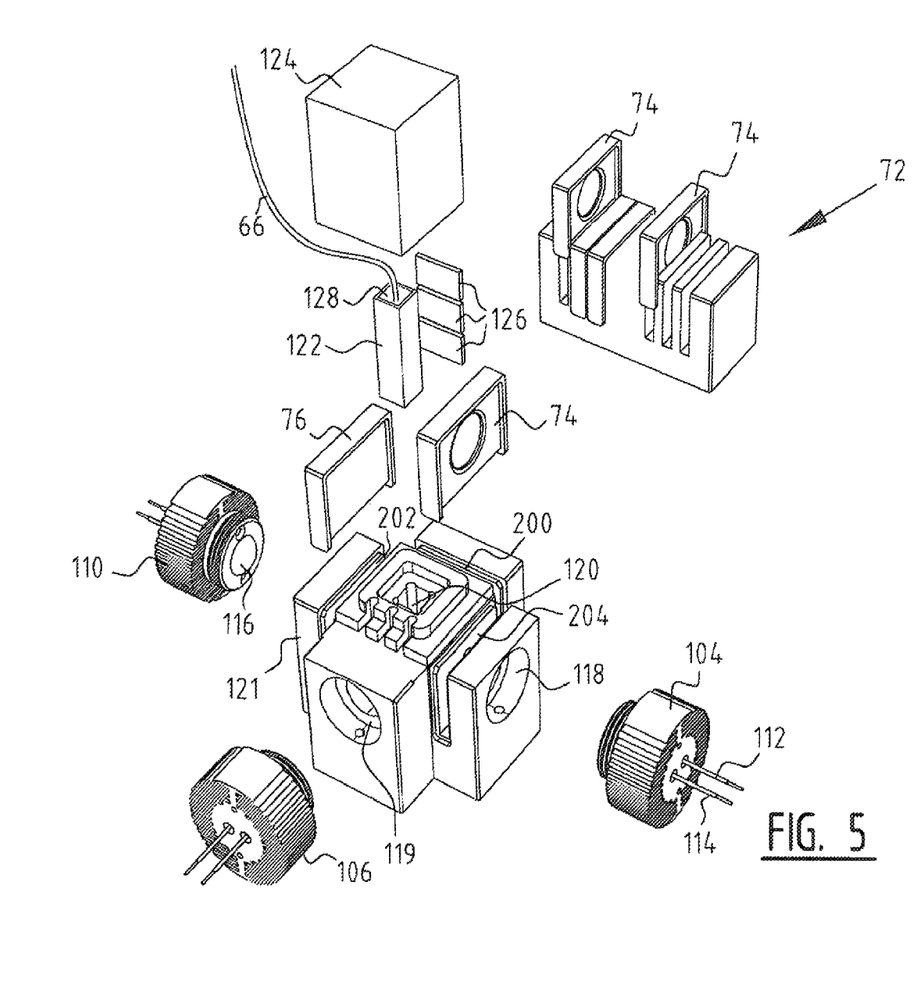
FIG. 5 shows the measurement means according to the first embodiment.

The measurement means 6 comprise a cuvette 122 comprising an inlet 128 for obtaining a fluid sample prepared by the fluid sample preparation means through connection 66. The cuvette 122 is situated in cavity 120.

The measurement means further comprise a light detector 126, which in this case is an array of CCD's. Further light detectors may be provided through holes 118, 119 or 121. The measurement means further comprise light source 104, 106, 110.

The measurement means further comprise light filters 74 which, when not in use, are placed in light filter container 72. If required, these filters can be placed in slots 200, 202 and/or 204. This can be performed manually or automatically.

Two examples of the system and the method according to the invention will be given, with reference to the first embodiment according to the FIGS. 1-5.

Example I

An application in a water treatment facility is considered. The automatic analysis system 2 obtains a sample from fluids or fluid streams of the water treating process. In this case, a sample of treated water is obtained through connection 40 from fluid stream 38. The main goal in this example is to detect if any micro-organisms are present in the fluids or fluid streams and, if this is the case, which micro-organisms and how much. By controlling the piston 10 with the motor 20 the sample is obtained from the source 38 into the fluid chamber 11 through connections 40, 62 and 68 and valves 60 and 68.

Several preparation steps are performed. The steps of preparation are performed according to an instruction set which can be programmed in hardware or software (not shown). The one or more preparation steps are selected from the group comprising filtration, dilution, concentration, heating, cooling, mixing, pumping, adding a processing fluid, adding a reagent and adding a fluorescent bead.

In the example of the water treatment facility, the first step comprises concentration of the micro-organism present in the fluid sample, since a small number of micro-organisms is expected to be present in the treated water. The fluid sample is pumped from the fluid chamber 11 through the filter 88 to the waste container 42 through connection 44. Since the filter comprises holes 90 of a diameter of 0.5 μm, which is the typical size of micro-organisms, the micro-organisms present in the fluid sample will remain at the same side of the filter 88 as the fluid chamber 11. More samples are obtained from the fluid or fluid stream 38 and a similar procedure is followed. In this manner more and more micro-organisms are retained in the fluid sample.

In a subsequent step a reagent is added to the fluid sample. Containers 12, 14, 16 can contain different reagents for different purposes. It is also possible to add a reagent at the other side of the filter through connection 36 from container 34. In stead of reagents the containers 12, 14, 16, 34 can also contain processing fluids and/or fluorescent beads. In this example, the reagent container comprises a micropump for pumping the reagent into the fluid chamber 11.

The preparation means comprises mixing means for mixing the reagent with the fluid sample. They further comprise heating and cooling means, such as a Peltier element, for temperature treatment of the fluid sample, for example when a reagent requires a certain activation temperature.

In a preparation step, fluorescent beads are added to the sample fluid. In the illustrated embodiment, the fluorescent beads are obtained from container 34.

The fluid sample is now prepared and ready for measurement and analysis. The piston 10 is activated with the motor 20 to push the fluid sample from the fluid chamber 11 through valve 68 and connection 66 to the measurement means 6.

With reference to FIG. 5, the fluid sample is transported to cuvette 122 through inlet 128. The measurement means comprise a light detector. In the embodiment of FIG. 5 the light detector comprises an array of CCDs 126. A photodiode is provided as an additional light detector, in hole 119 in stead of LED 106. Light emitting diodes 104 and 110 emit ultraviolet light. The reagents of the prepared fluid sample respond to the ultraviolet light by emitting fluorescent light. The fluorescent light is in the visible spectrum. A light filter 74 which blocks ultraviolet light is placed in slot 200. Therefore, no ultraviolet light will be detected by light detector 126.

The intensity of the detected light can be related to the quantity of micro-organisms present. This requires a type of calibration, since the response of the measurement means may vary due to external and internal influences, such as ambient temperature. In this example, the calibration is performed using the fluorescent beads.

The fluorescent beads emit light of a known intensity and known wavelength. It is possible that the beads require excitation by a light source provided in the measuring module 6 before they emit light. The fluorescent beads can comprise, for example, latex beads.

For example, the fluorescent beads can be obtained from containers 12, 14, 16, 26 and/or 34. The beads are added to the fluid sample after which a calibration step is performed. For example, they are added by the preparation means or manually. Furthermore adding means can be provided to add the beads to the cuvette of the measurement means.

The light emitted by the fluorescent beads is detected, wherein a light filter in front of the detector is used. The light filter blocks light of different wavelengths than the wavelength emitted by the beads. Therefore, only the light emitted by the beads is detected. The system is calibrated by relating the measured light intensity of the light emitted by the beads to the expected light intensity.

It is noted that the calibration measurement and the actual measurement can be performed at the same time if more than one detector is provided, wherein one detector detects the light emitted by the beads only. In this example, the calibration step and the actual measurement are performed subsequently.

The analysis step is performed automatically by a processing unit (not shown). In the example one of the analysis steps comprises calculation of the amount of the micro-organisms present in the fluid or fluid stream. This calculation takes into account that the fluid sample is obtained through a concentration step in which the micro-organism content of several samples were concentrated in a single fluid sample.

A further analysis step comprises scaling the measurements to the results of the calibration measurements to obtain results which are independent of varying external and internal influences.

On the basis of the measurements it is for example possible to conclude that the amount of *legionella* in the treated water is unacceptably high. The system can send a control signal using the communication means, to interact with the process. In this case an alarm is raised and, if necessary, several valves can be closed so that the contaminated water does not leave the factory. The system further communicates the measurement and analysis results to an operator for informing the operator on the contamination and providing all the details.

Example II

An application is considered wherein the fluids or fluid stream comprises milk. Since milk is a non-transparent fluid, which would complicate light measurements, one of the preparation steps comprises dilution of the sample obtained from the fluid source.

The goal is to perform an adenosine triphosphate (ATP) test using a luceferin. A sample of milk is obtained from the process through connections 32 or 40. It is noted that in this case also connection 32 can be used, although the sample will pass through the filter 88 before entering the fluid chamber 11, since it does not matter that any micro-organisms will be retained by the filter. The milk is obtained from the fluids or fluid streams 30 or 38 by moving the piston 10 by using motor 20. The piston is moved over only a part of its length such that it becomes only partly filled. The solvent is obtained from the source 22 which in this example is a water tap. The water flows through connection 24 and dilutes the milk present in fluid chamber 11. If further dilution of the fluid sample is necessary the piston can be partly emptied through connection 44 in waste container 42. Subsequently, more solvent water from container 22 is obtained through connection 24 and the fluid sample is diluted further.

In this example, container 12 contains a bioluminescent reagent for the ATP measurement. The bioluminescent reagent is obtained through connection 46 and mixed with the diluted milk in a watery solution in the fluid chamber 11 by mixing means (not shown). If necessary, the heating and cooling means 13 keep the milk in the watery solution at the right temperature, for instance preventing the denaturization of the proteins.

The fluid sample has now been prepared and is ready for measurement and analysis. Valve 64 is controlled such that the fluid sample can flow through connections 68 and 66 from the piston 10 to the measurement means 6.

The prepared fluid sample enters the cuvette 122 through connection 66 and inlet 128. As a first check, the transparency of the watery milk solution is measured in the measurement means. This is done by irradiating the cuvette comprising the fluid sample by LED 106 and measuring the light using detectors 126. The intensity of the light is related to the total absorption by the fluid sample.

It is noted that this measurement can be calibrated using a sample which contains only the solvent. This calibration run can be performed before or after the measurements of the watery milk solution. If the watery milk solution is too opaque for performing accurate measurements, a new sample can be prepared which is more diluted than the measured fluid sample.

If the check is passed, i.e. the prepared sample is usable for further measurements, the sample is irradiated by LED 104, LED 106 and/or LED 110. In this example, LED 104 is a violet/ultraviolet LED, LED 106 is a red LED and LED 110 is a green LED. The detector is provided with a green light filter 74. One measurement is performed, after which the green light filter is replaced by a red light filter and subsequently another measurement is performed. In this example, the light filters are interchanged manually, however it is also possible to handle this automatically. After the measurements, the fluid sample is discharged through the outlets (not shown) to a waste container or drain.

The analysis step comprises relating the measurements to the preparation and the calibration measurements. The fluid sample was obtained by diluting it at least one time. This information is used to calculate the concentration of ATP in the fluid or fluid stream from the results of the measurements using the diluted fluid sample. The calibration of the detected light intensity proceeds as in Example I. This results in a quantification of the amount of ATP in the milk obtained from the fluids or fluid streams 38 and/or 30.

The results of the analysis can be communicated using the communication means. When an increased amount of ATP is detected, indicating a possible high level of micro-organisms an indicator signal is sent to an operator. The system may also interrupt the process from which the sample was obtained automatically by sending an appropriate control signal.

Figure 6:
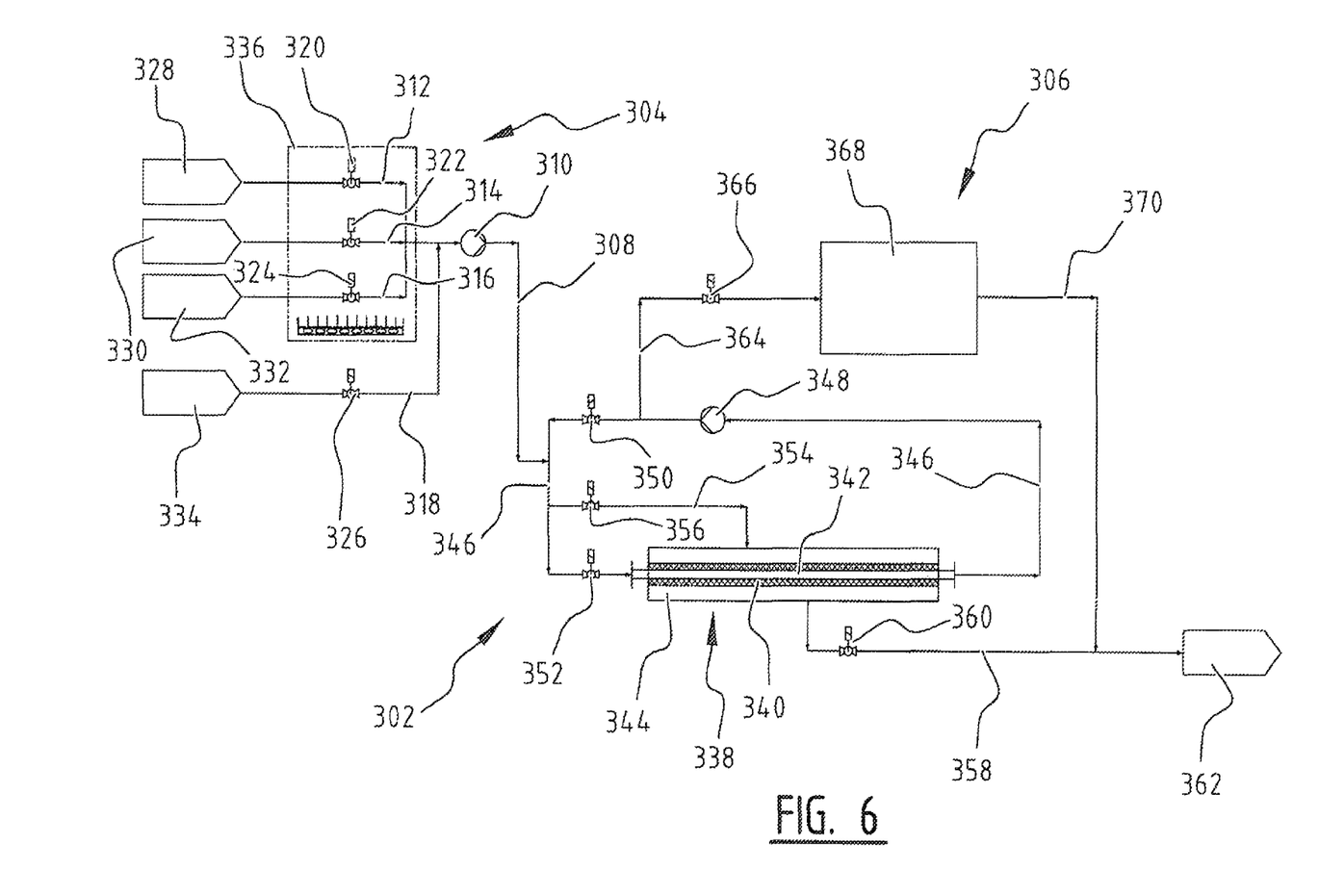
FIG. 6 shows a schematic representation of a second, currently preferred, embodiment of the automatic analysis system according to the invention.
Figure 7:
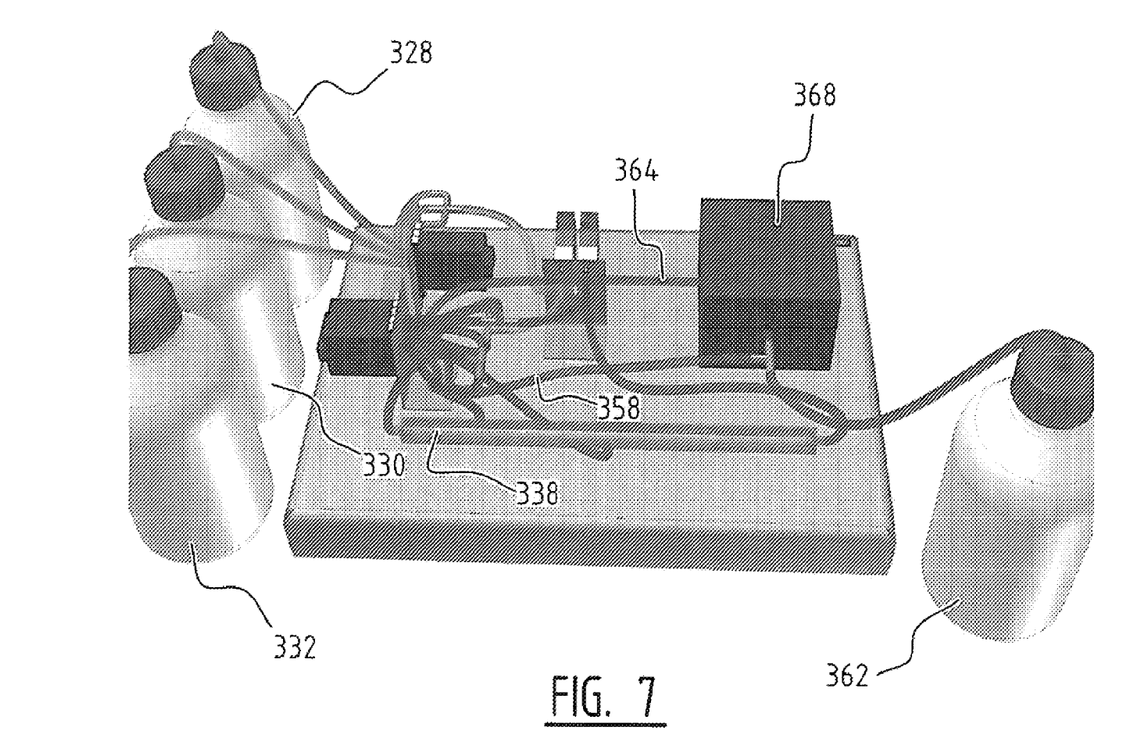
FIG. 7 shows a 3D drawing of the automatic analysis system according to the second embodiment of FIG. 6.

A second, currently preferred embodiment, of the system according to the invention is schematically represented in FIG. 6 and shown in a 3D representation in FIG. 7.

The system comprises a preparation circuit part 302, a input part 304 and a measurement part 306.

The input part 304 of the system comprises an inlet conduit 308 connecting the input part 304 to preparation circuit part 302. Inlet conduit 308 is connected via pump 310 with four conduits 312, 314, 316, 318, which are provided with controllable valves 320, 322, 324, 326 respectively to enable obtaining a fluid from fluid stream 328 or containers 330, 332, 334.

Conduit 312 is connected to the fluid to be analyzed, represented by fluid stream 328, via valve 320.

Conduit 314 is connected to a container 330 containing buffer fluid, such as purified water, via valve 322.

Conduit 316 is connected to a container 332 containing a reagent or colouring agent, via valve 324.

Conduit 318 is connected to a container 334 containing a disinfection fluid, such as chlorine, via valve 326.

Input part 304 further comprises an UV disinfection block 336 for optional disinfection of the fluids from stream 328 or containers 330, 332. The disinfection is carried out by means of UV-LEDs.

The preparation circuit part 302 comprises a crossflow filter 338 which comprises a permeable sheath 340 of a ceramic material, enclosing an inner channel 342 of 0.2 μm diameter. The permeable sheath 340 is covered by outer tubing 344, which is of a plastic material. The length of filter 338 is approximately 10 cm.

The fluid can flow through inner channel 342, i.e. in the longitudinal direction of filter 338. When an overpressure is created, the fluid is forced through the permeable membrane 340, i.e. in the transverse direction of filter 338. The permeable membrane 340 filters the fluid forced through it. The flux is 100 $l^{-1}m^2h^{-1}$.

The crossflow filter 338 is provided in conduit loop 346. The loop 346 comprises a pump 348 to circulate the fluid in the loop. The loop has a volume of 5 ml.

Conduit loop 346 further comprises valves 350, 352 and branch 354, which is opened or closed by means of valve 356. Branch 354 enables flowing a fluid through crossflow filter in the transverse direction. When circulating fluid in loop 346, valve 356 is in a closed state to block branch 354.

Branch 354 continues at the opposite side of filter 338 in conduit 358, which contains valve 360. Conduit 358 is connected to waste container 362. Alternatively, a waste stream is provided.

A further branch 364 of loop 346 connects loop 346 via valve 366 with detector 368. Detector 368 is a modular detector, preferably a light detector, for instance a fluorescence detector.

Detector 368 is connected to waste container 362 via conduit 370.

A process for analyzing a fluid or fluid stream using the currently preferred embodiment as illustrated in FIGS. 6-7 will be explained in further detail.

A sample of the fluid or fluid stream to be analyzed is obtained by opening valve 320 and activating pump 310. Valve 350 and valve 352 are also open, while the other valves remain closed. Pump 350 circulates the sample in loop 346, wherein the fluid passes through the crossflow filter 340 in the longitudinal direction. The loop 346 is completely filled with sample fluid.

Purified water is added by closing valve 320 and opening valves 322, 360. Pumping buffer fluid into conduit loop 346 forces the sample fluid through filter 338, after which it will flow to waste container 362. Micro-organisms and biological substances are retained in the circulating fluid by filter 338. This way a clear fluid is obtained comprising the micro-organisms and biological substances from the sample of the fluid to be analyzed.

Subsequently, a colouring agent is obtained from container 332 and added to the fluid in conduit loop 346 by opening valve 314. Valves 350, 352 and 360 remain open. Valve 314 is opened for a short time, since a small amount of (concentrated) colouring agent suffices.

The colouring agent is mixed with the fluid by circulating the fluid in loop 346 for a certain amount of time. This is achieved by closing all valves except 350 and 352.

After the mixing step, excess colouring agent is removed by "pushing" it to waste container 362 using buffer fluid from container 330. This is achieved by opening valves 322 and 360. Valve 350 and valve 352 remain opened. It is noted that the colouring agent is not retained by filter 338. The result is that excess colouring agent, which is dissolved in the fluid but not attached to the micro-organisms or biological substances, is flushed to waste container 362. The fluid in loop 346 contains coloured micro-organisms or biological substances in a clear fluid.

Next, the prepared fluid is transported to detector 368 by closing valves 360 and 350 and opening valves 322, 352 and 366. Buffer fluid from container 330 pushes the fluid via part of conduit loop 346 to branch 364, towards detector 368.

Detector 368 comprises a transparant flowthrough cuvet with a 1 ml volume and a UV light source (now shown). UV light irradiates the dyed particles which re-emit, reflect or absorb light. This light is detected by a photodetector. The light bundle has a relatively small width and a relatively high intensity. The duration of the measurement is typically 100-1000 s. The frequency of detected pulses corresponds to the concentration of particles to be detected.

Optionally, the measurement can be performed five times in a row, since the loop 346 contains 5 ml of prepared fluid and the detector 368 performs a measurement using 1 ml fluid.

After measurement, the fluid flows to waste container 362 via conduit 370.

A further step can comprise cleaning the filter by using a backwash procedure. All valves are closed, except valves 326, 352 and 360. Chlorine is obtained from container 334 and flows via conduits 318, 308 into branch 354, through filter 338 and into waste container 362.

A further cleaning step can comprise opening valves 350, 352 and/or valve 366, to clean conduit loop 346 and detection part 306 as well. Furthermore, an additional step can comprise flushing the conduits using the buffer fluid to remove all chlorine solution from the system.

The process steps described above are depicted in table 1 below. This table indicates which valves are opened and closed in each step: an empty circle representing an open valve and a filled circle representing a closed valve.

TABLE 1

Valves open and closed in different process steps

| step | 320 | 322 | 324 | 326 | 350 | 352 | 356 | 360 | 366 |
|---|---|---|---|---|---|---|---|---|---|
| obtain sample | ○ | ● | ● | ● | ○ | ○ | ● | ● | ● |
| add buffer fluid | ● | ○ | ● | ● | ○ | ○ | ● | ○ | ● |
| add coloring agent | ● | ● | ○ | ● | ○ | ○ | ● | ○ | ● |
| circulate/mix | ● | ● | ● | ● | ○ | ○ | ● | ● | ● |
| remove excess colour using buffer fluid | ● | ○ | ● | ● | ○ | ○ | ● | ○ | ● |
| fluid to detector | ● | ○ | ● | ● | ● | ○ | ● | ● | ○ |
| clean filter | ● | ● | ● | ○ | ● | ● | ○ | ○ | ● |

It is noted that in the system and method according to the invention, also an alternative detector may be used instead of a detector using light, for instance a detector using the impedance of the fluid.

The present invention is by no means limited to the above described preferred embodiments thereof. The rights sought are defined by the following claims, within the scope of which many modifications can be envisaged. It is thus possible for instance to make a combination of the measures from the different embodiments. It is for instance possible to use the automatic analysis system and method for use thereof according to the invention in a lab setting, not necessarily in-process. It is for instance also possible to provide additional light detectors, for example in holes 118, 119 and/or 121 instead of light sources. Furthermore, the detector in the first embodiment can be used in the second embodiment and vice versa. The use of fluorescent beads is not restricted to the first embodiment and can also be applied in the second embodiment.

The invention claimed is:

1. A method for detecting micro-organisms and/or biological substances in a fluid, the method comprising:
   (a) introducing a sample from the fluid into a conduit loop through a first inlet by opening a first valve, wherein the conduit loop comprises a cross flow filter comprising an elongated permeable sheath enclosing an inner channel, configured such that during use fluid flows through the inner channel of the cross flow filter in a longitudinal direction thereof during circulation of fluid in the conduit loop;
   (b) circulating the sample in the conduit loop using a pump;
   (c) simultaneously introducing a first volume of buffer fluid from a buffer fluid source into the conduit loop by opening a second valve of a second inlet while the sample is being circulated in the conduit loop, such that the sample flows multiple times through the inner channel of the cross flow filter in a longitudinal direction of the filter while circulating in the conduit loop and is simultaneously, at least partially forced out of the inner channel and through the elongated permeable sheath in a direction transverse to the longitudinal direction of the filter so that the filter retains micro-organisms and/or biological substances of the sample in the conduit loop;
   (d) introducing a FISH reagent from a FISH reagent source into the conduit loop by opening a third valve of a third inlet to produce a prepared fluid sample;
   (e) removing an excess volume of FISH reagent from the conduit loop by introducing a second volume of buffer fluid into the conduit loop by opening the second valve while the excess volume of FISH reagent is being circulated in the conduit loop so as to remove the excess volume of FISH reagent from the inner channel of the cross flow filter to create a sample consisting of colored micro-organisms and/or biological substances in a clear fluid;
   (f) transporting the prepared fluid sample through a fourth valve of an outlet of the conduit loop to a fluorescence detector by opening the fourth valve; and
   (g) detecting light emitted by the prepared fluid sample using a fluorescence detector to detect micro-organisms and/or biological substances in the fluid,
   wherein circulating the sample in the conduit loop using the pump comprises transporting at least a portion of the fluid from the cross flow filter to a waste container via a conduit comprising an inlet that is disposed outside of the elongated permeable sheath of the cross flow filter and perpendicular relative to the longitudinal flow through the inner channel of the cross flow filter.

2. The method according to claim 1, wherein during step (a) the second valve, the third valve and the fourth valve are closed.

3. The method according to claim 1, wherein during step (c) the first valve, the third valve and the fourth valve are closed.

4. The method according to claim 1, wherein during step (d) the first valve, the second valve and the fourth valve are closed.

5. The method according to claim 1, wherein during step (e) the first valve, the third valve and the fourth valve are closed.

6. The method according to claim 1, wherein during step (b) the first valve and the third valve are closed.

7. The method according to claim 6, wherein during step (f) the second valve is open to introduce buffer fluid into the conduit loop, which pushes the prepared fluid sample via the outlet conduit to the fluorescence detector.

8. The method according to claim 1, wherein step (d) comprises, after introducing FISH reagent into the conduit loop, mixing the sample and the FISH reagent by circulating the fluid in the conduit loop for a predetermined time while the first valve, second valve, third valve and fourth valve are closed.

9. The method according to claim 1, further comprising after step (g) transporting the fluid to the waste container.

10. The method according to claim 1, wherein the conduit loop is further connected to a container comprising a disinfection fluid via a fifth inlet conduit comprising a fifth valve, the method further comprising cleaning the cross flow filter, wherein the first valve, the second valve, the third valve and fourth valve are closed and the fifth valve is open.

11. The method according to claim 10, further comprising flushing the conduit loop using the buffer solution to remove the disinfection fluid from the system.

12. The method according to claim 1, further comprising the steps of:
    adding fluorescent beads to the fluid sample before performing a calibration measurement;
    performing the calibration measurement by measuring the intensity of the light emitted by the fluorescent beads; and
    correcting measurements according to the relation between the light intensity measured in the calibration measurement and an expected light intensity.

13. The method according to claim 1, further comprising measuring a total amount of micro-organisms and/or biological substances.

14. The method according to claim 1, further comprising measuring an amount of one or more types of micro-organisms and/or biological substances.

* * * * *